United States Patent [19]
Yasuki et al.

[11] Patent Number: 5,137,575
[45] Date of Patent: Aug. 11, 1992

[54] CHROMATIC PIGMENTS COMPRISING A COLORING METAL OXIDE COATING ON TRANSPARENT TITANIUM OXIDE CORE PARTICLES OF 0.01 TO 0.1 MICRON SIZE

[75] Inventors: Takashi Yasuki; Shunji Idei, both of Okayama, Japan

[73] Assignee: Tayca Corporation, Osaka, Japan

[21] Appl. No.: 530,399

[22] Filed: May 30, 1990

[30] Foreign Application Priority Data

Jun. 2, 1989 [JP] Japan .................. 1-141624

[51] Int. Cl.[5] .................. C09D 5/36; C09D 5/29; C09D 1/36; C09D 3/06
[52] U.S. Cl. .................. 106/441; 106/439; 106/440
[58] Field of Search .................. 106/439, 440, 441

[56] References Cited

U.S. PATENT DOCUMENTS

| | | | |
|---|---|---|---|
| 2,257,278 | 9/1941 | Schaumann | 106/440 |
| 3,418,147 | 12/1968 | Fields | 106/439 |
| 4,390,374 | 6/1983 | Balducci et al. | 106/440 |
| 4,753,829 | 6/1988 | Panush | 427/38 |
| 4,976,787 | 12/1990 | Ho et al. | 106/440 |

FOREIGN PATENT DOCUMENTS 0472605 9/1937 United Kingdom ............ 106/439

Primary Examiner—William R. Dixon, Jr.
Assistant Examiner—Scott L. Hertzog
Attorney, Agent, or Firm—Burns, Doane, Swecker & Mathis

[57] ABSTRACT

$TiO_2$-based chromatic pigments are provided by coating core particles of $TiO_2$ having a mean particle size from 0.01 to 0.1 μm with a layer of metal oxide of Ni, Co, Ce, Cu, Cr, Mn, V, W or a mixutre thereof.

15 Claims, 4 Drawing Sheets

① STARTING TiO2
② NiO COATED TiO2

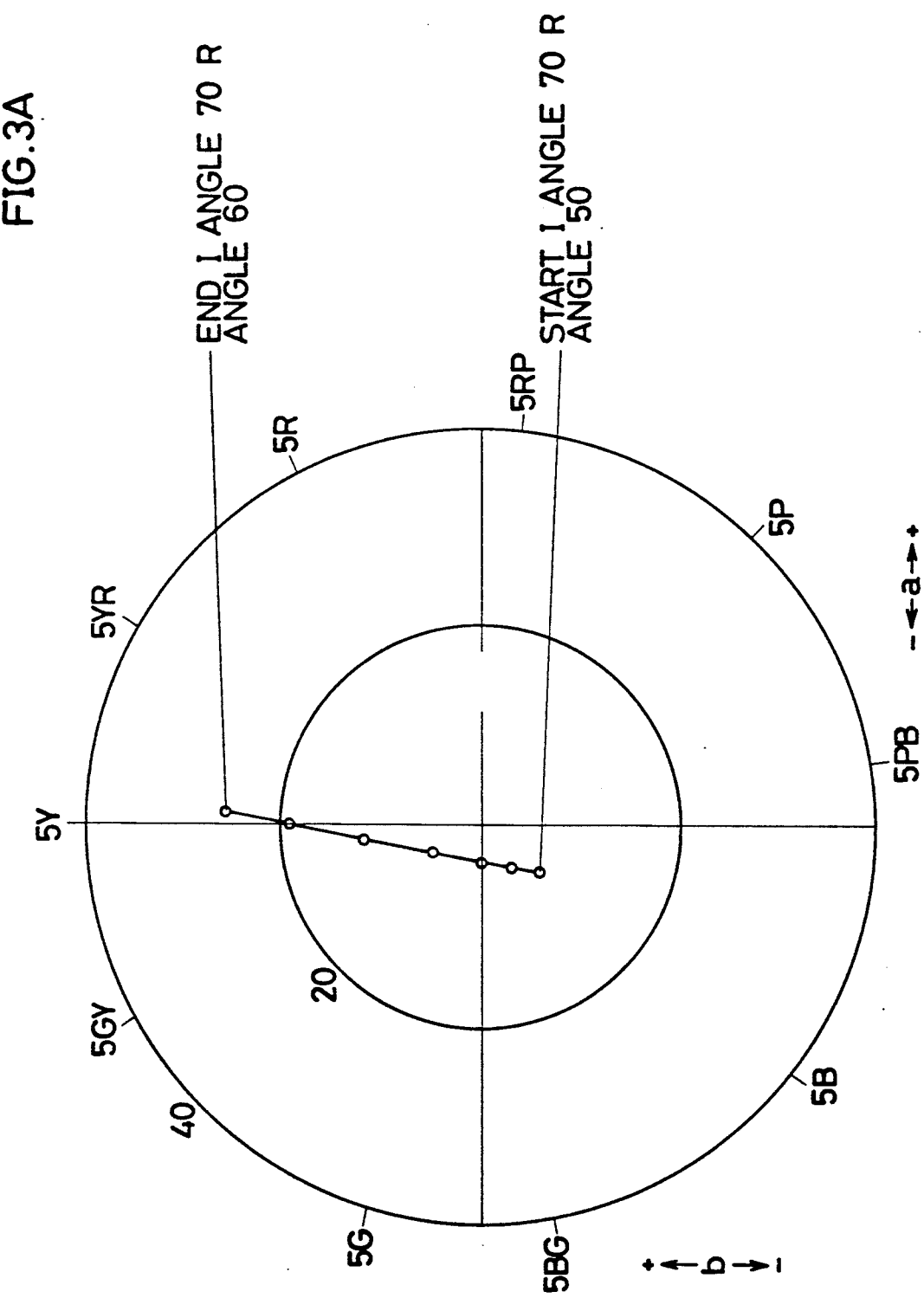

CHROMATIC PIGMENTS COMPRISING A COLORING METAL OXIDE COATING ON TRANSPARENT TITANIUM OXIDE CORE PARTICLES OF 0.01 TO 0.1 MICRON SIZE

BACKGROUND OF THE INVENTION

This invention relates to titanium dioxide-based chromatic pigments useful as a colorant of paints, printing inks, plastics, cosmetics and the like.

Titanium dioxide particles are well-known as a white pigment and have been used in the paint, plastics, cosmetics and many other industries. The pigment grade $TiO_2$ particles generally have a mean particle size of about 0.2–0.3 $\mu$m. Finer particles of $TiO_2$ having a mean particle size less than 0.1 $\mu$m exhibit different optical properties from the $TiO_2$ pigments. They are almost colorless or transparent to visible light but selectively block the passage of UV light therethrough. Accordingly, they find uses as UV blocking agents rather than chromatic pigments in the paint, plastics, cosmetics and other industries. In addition, U.S. Pat. No. 4,753,829 discloses the incorporation of $TiO_2$ microparticles into the base coat of multi-layer metallic coatings to promote "down-flop" effect.

$TiO_2$ based chromatic pigments have been known including those disclosed in U.S. Pat. No. 2,257,278 and Japanese Patent Publication No. 25685/72. They are generally solid solutions of coloring oxides of metals such as Sb, Ba, Ni and Co in a $TiO_2$ lattice. These pigments are produced by intimately mixing $TiO_2$ and the coloring metal oxides or oxide precursors, calcining the mixture at a temperature of 1000°–1300° C., cooling and grinding the resulting products. Pigments thus produced are very hard and it is difficult to grind them to a mean particle size of less than 0.1 $\mu$m.

Accordingly, needs exist for chromatic pigments useful as a colorants of paints, plastics, cosmetics and the like while retaining at the same time most of beneficial properties of $TiO_2$ microparticles such and UV blocking and down flop promoting properties.

SUMMARY OF THE INVENTION

In one aspect of the present invention, there is provided a chromatic pigment comprising core particles of $TiO_2$ having a mean particle size of 0.01 to 0.1 $\mu$m coated thereon with a layer of an oxide of Ni, Co, Ce, Cu, Cr, Mn, V, W or a mixtue of these oxides.

In another aspect of the present invention, there is provided a method for producing a chromatic pigment comprising the steps of suspending $TiO_2$ microparticles having a mean particle size of 0.01 to 0.1 $\mu$m in an aqueous medium, adding a water-soluble compound of Ni, Co, Ce, Cu, Cr, Mn, V, W or a mixture of said compound, hydrolyzing said metal compound and depositing the resulting metal hydroxide on said $TiO_2$ particles, recovering and calcining the resulting product at a temperature of 300° C. to 800° C.

BRIEF DESCRIPTION OF DRAWINGS

FIGS. 3A and 3B are chromaticity diagrams of multi-layer metallic coatings incorporating the pigment of the present invention and conventional $TiO_2$ microparticles, respectively.

DETAILED DISCUSSION

Figure 1:
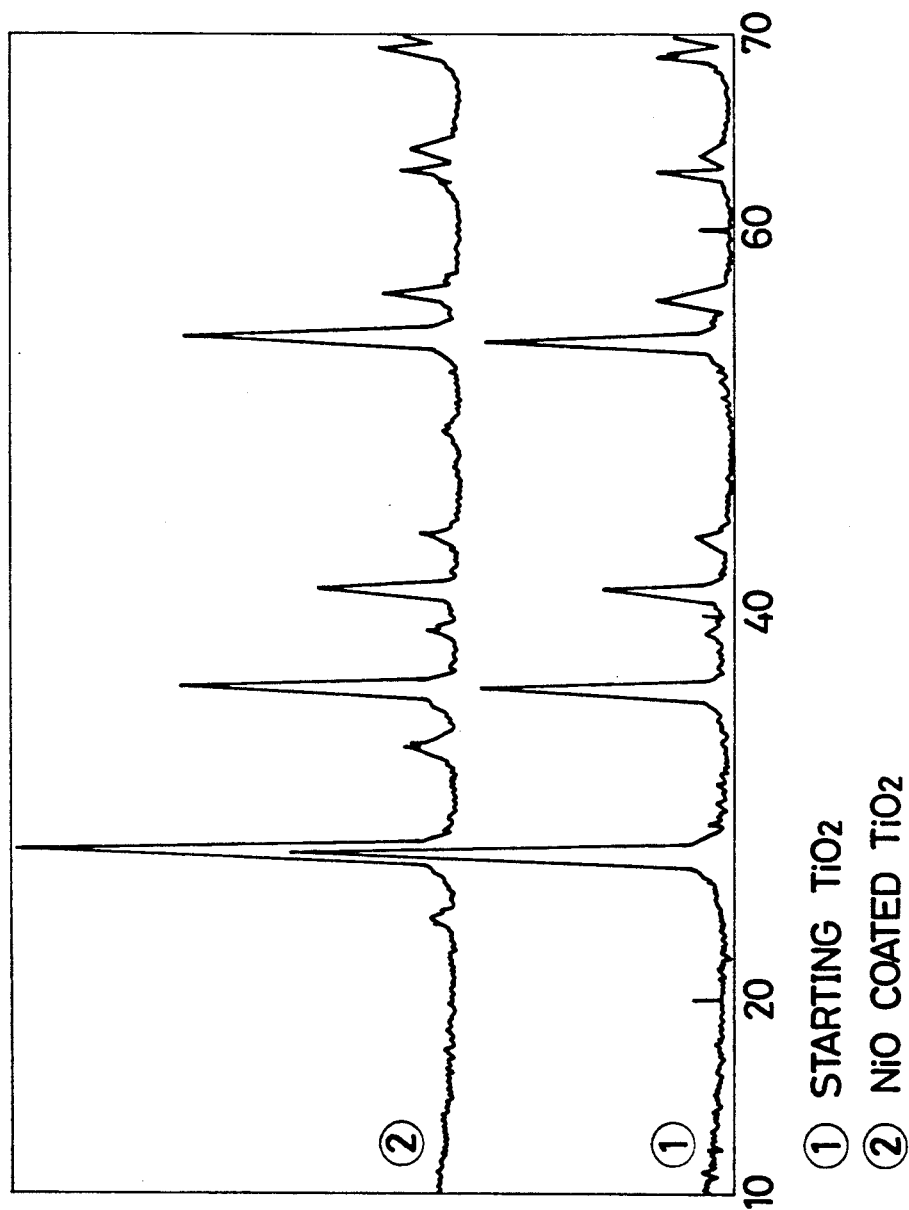
FIG. 1 shows X-ray diffraction patterns of $TiO_2$ microparticles before and after coating with nickel oxide.

The chromatic pigment of the present invention comprises core particles $TiO_2$ having a mean particle size of 0.01 to 0.1 $\mu$m and a colored metal oxide layer covering the core particles.

The starting $TiO_2$ microparticles may be produced by the well-known colloid chemical process or the chemical concentration process. Their crystallographic structure may be anatase, rutile or a mixture thereof. Commercially avilable $TiO_2$ microparticles having a protective coating of $SiO_2$, $Al_2O_3$ or $ZrO_2$ on the $TiO_2$ core particles may also be used. Particles greater than 0.1 $\mu$m have a greater opacity than desirable to use as the starting material of the pigment of the present invention.

The starting $TiO_2$ microparticles are suspended in water preferably at a concentration less the 300 g/L, typically at a concentration of 200 g/L. To the suspension is added a water-soluble metal compound with stirring. The color characteristic of final pigment is determined by the particular metal species employed. To this end, Ni, Ce, Cr, V and W give yellow, Co gives green, Cu and Mn give black. Mixtures of two metal species give an intermediate color. Examples of water-soluble compounds include chlorides, sulfates and nitrates of Ni, Ce, Co, Cu, Cr and V, and ammonium tungstate. The ratio of the water-soluble metal compound to $TiO_2$ microparticles is such that the final pigment particles are coated with 1 to 30% as $NiO$, $CeO_2$, $CoO$, $CuO$, $Cr_2O_3$, $MnO_2$, $V_2O_5$ or $WO_2$ by weight of the starting $TiO_2$ microparticles. The color intensity of the final pigment is directly proportional to the amount of coating. Therefore, the exact amount of water-soluble metal compounds to be added will depend upon the color intensity as desired.

After the addition of water-soluble metal compounds, the suspension is heated to a temperature from 40° C. to the boiling point thereof for at least 30 minutes with stirring. Then the suspension is gradually neutralized to a pH 8–9 with a suitable base or acid such as aqueous ammonia, sodium hydroxide, hydrochloric acid, sulfuric acid or nitric acid to hydrolyze the metal salt and deposit the resulting metal hydroxide on the $TiO_2$ microparticles. After neutralization, the suspension is allowed to stand for at least 30 minutes and then filtered. The resulting filter cake is washed with water and dried at 100°–150° C. to obtain $TiO_2$ microparticles coated with a metal hydroxide layer. Color development takes place when calcining the above product at a temperature above 300° C. for 0.5 to 4 hours. Care should be taken in this step to prevent the pigment particles from sintering to large hard aggregates. Experiments have shown that about 800° C. is the upper limit to maintain the desired particle size and transparency in the final pigment. Experiments have also shown that the addition of a small amount of calcium or aluminum salts, silicates, phosphates, antimony salts, zirconium salts, tin compounds, zinc compounds or niobium compounds to the suspension prior to the neutralization step is effective for the prevention of sintering into large aggregates, color development, particle size-regulating and other purposes. This calcining step may be carried out in any conventional furnace of tunnel, electrical and othe types.

The pigment thus produced may be further coated with one or more hydrated oxides of Si, Al, Zn, Sn and like metals to enhance weatherability, dispersibility and other properties.

As can be easily appreciated, the pigment of the present invention has unique optical properties compared with prior art $TiO_2$-based colored pigments such as titanium yellow. The pigment has a sufficiently fine particle size to selectively transmit visible light while blocking the passage of UV light as do $TiO_2$ microparticles. This is because the pigment is calcined at an elevated temperature at which the pigment particles are not sintered to large hard aggregates. The color characteristics of the pigment of the present invention vary depending upon the metal species and the amount of colored metal oxide layer from pastel to deep tone and find a variety of uses in the paint, plastics, cosmetics and other industries.

The pigment of the present invention is particularly useful to impart multilayer metallic coatings comprising a metallic base coat and a clear top coat with down-flop effect by incorporating the pigment of this invention into the base coat as taught by U.S. Pat. No. 4,753,829.

Such multilayer metallic coatings are well-known in the art to finish, for exmaple, automobile bodies. The base coat composition may comprise (a) 20 to 40% by weight of a film-forming synthetic resin; (b) 1 to 10% by weight of a metallic or metallic-like pigment; (c) 1 to 15% by weight of the colored $TiO_2$ microparticle pigment of the present invention; and (d) the balance of an organic volatile solvent for said film-forming synthetic resin.

The film-forming systhetic resin (a) may be any of the polymers known to be useful in coating compositions such as acrylic polymers, alkyd resins and polyester resins having cross-linkable functional groups such as hydroxy and/or carboxyl groups. Cross-linkers such as melamine resins and polyisocyanate compounds, and catalysts for the reaction of the cross-linkers with the film-forming polymers such as sulfonates and tin compounds, where present, should be considered as being part of said film-forming synthetic resins.

The metallic or metallic-like pigment may be any of conventional pigments such as aluminum flake, bronze flake, $TiO_2$-coated mica flake, $TiO_2$-coated micaceous iron oxide flake and the like. They preferably have an aspect ratio from 10 to 100. These metallic or metallic-like pigments may be used in combination with conventional non-metallic pigments such as carbon black, iron oxide, perylene pigments and the like.

The organic volatile solvnets may be any of liquids which are conventionally used as polymer solvents in coating compositions such as aliphatic or aromatic hydrocarbons, ester, ketones, alcohols and the like.

The clear topcoat composition to be applied on the base coat may be generally the same as the base coat composition except that it does not contain pigments and thus transparent.

In use, the base coat composition is applied on a suitable substrate such as antomobile bodies to a film thickness of, for example, 10 to 50 microns and then the clear topcoat compositions is applied thereon preferably wet-on-wet followed by baking both coats simultaneously.

The multilayer metallic coatings incorporating the pigment of this invention exhibit higher down-flop effect and chromaticity than the corresponding coatings incorporating conventional colorless or white $TiO_2$ microparticles. Particularly, the pigment of this invention having yellowish colors gives the multilayer coatings which have warmer flop (color viewed on the same side as the incident light at a near angle) and more intense golden face (color viewed on the opposite side to the incident light) than the conventional colorless or white $TiO_2$ microparticles. Furthermore, the pigment of this invention have a number of unique optical properties including adequate degrees of light scattering, refracting and transmitting properties owing to the $TiO_2$ core microparticles. These unique properties are not found in conventional color pigment microparticles such as iron oxide microparticles.

The following examples are offered for illustrative purposes only.

EXAMPLE 1

1400 g of rutile type titanium dioxide microparticles having a mean particle size of 15 nm was dispersed in water at a concentration of 200 g/L. To the suspension was added 496 g of nickel sulfate as $NiSO_4 \cdot 6H_2O$ with stirring. After heating the suspension to 80° C., an amount of 50 g/L aqueous solution of sodium hydroxide was added over 60 minutes until the pH of the suspension became 9. Then the suspension was allowed to stand for 30 minutes and filtered. The resulting filter cake was washed with 7 L of water, centrifuged, dried at 120° C., calcined in an electrical furnace at 600° C. for 2 hours, and pulverized in an atomizer.

Properties of the resulting pigment are shown in Table 1. X-ray diffraction patterns of the titanium dioxide microparticles before and after coating with nickel oxide are shown in FIG. 1.

EXAMPLE 2

The process of Example 1 was repeated except that the pigment was calcined at 700° C.

EXAMPLE 3

The process of Example 1 was repeated except that amount of nickel sulfate was decreased to 250 g.

EXAMPLE 4

The process of Example 1 was repeated except that 672 g of cerium sulfate as $Ce_2(SO_4)_3 \cdot 8H_2O$ was replaced for 496 g of $NiSO_4 \cdot 6H_2O$.

EXAMPLE 5

The process of Example 1 was repeated except that 529 g of cobalt sulfate as $CoSO_4 \cdot 7H_2O$ was replaced for 496 g of $NiSO_4 \cdot 6H_2O$.

EXAMPLE 6

The process of Example 1 was repeated except that 472 g of copper sulfate as $CuSO_4 \cdot 5H_2O$ was replaced for 496 g of $NiSO_4 \cdot 6H_2O$.

EXAMPLE 7

The process of Example 1 was repeated except that 200 g of chromium chloride as $CrCl_3 \cdot 6H_2O$ was replaced for 496 g of $NiSO_4 \cdot 6H_2O$.

EXAMPLE 8

The process of Example 1 was repeated except that 319 g of manganese sulfate was $MnSO_4 \cdot H_2O$ was replaced for 496 g of $NiSO_4 \cdot 6H_2O$.

EXAMPLE 9

The process of Example 1 was repeated except that 515 g of vanadium sulfate as $VSO_4 \cdot 7H_2O$ was replaced for 496 g of $NiSO_4 \cdot 6H_2O$.

EXAMPLE 10

The process of Example 1 was repeated except that 535 g of ammonium tungstate as $(NH_4)_2WO_4$ was replaced for 496 g of $NiSO_4 \cdot 6H_2O$.

EXAMPLE 11

The process of Example 1 was repeated except that 132 g of antimong chloride as $SbCl_3$ was used in combination with 496 g of nickel sulfate as $NiSO_4 \cdot 6H_2O$.

COMPARATIVE EXAMPLE

The $TiO_2$ microparticles used as starting material in Example 1 were calcined in an electrical furnace at 600° C. for 2 hours and then pulverized in an atomizer to give white $TiO_2$ microparticles.

TABLE 1

| Example | Properties of pigments Amount of coating, % | Specific surface area, m²/g | Munsell value H | V | C |
|---|---|---|---|---|---|
| 1 | $NiO/TiO_2 = 9.7$ | 45.7 | 5.5 Y | 8.8 | 4.4 |
| 2 | $NiO/TiO_2 = 9.7$ | 29.2 | 5.1 Y | 8.8 | 4.3 |
| 3 | $NiO/TiO_2 = 4.9$ | 45.0 | 5.3 Y | 8.8 | 3.8 |
| 4 | $CeO/TiO_2 = 4.8$ | 45.2 | 5.0 Y | 8.8 | 5.3 |
| 5 | $CoO/TiO_2 = 9.8$ | 45.9 | 2.1 BG | 7.7 | 1.4 |
| 6 | $CuO/TiO_2 = 9.7$ | 45.8 | 2.9 YR | 5.3 | 0.5 |
| 7 | $Cr_2O_3/TiO_2 = 4.0$ | 44.7 | 1.2 Y | 7.5 | 4.8 |
| 11 | $NiO/TiO_2 = 9.7$ $Sb_2O_3/TiO_2 = 5.8$ | 45.8 | 6.4 Y | 8.8 | 4.2 |

Amount of Coating: Chemical analysis.

Specific surface area: $N_2$ gas adsorption method using Model SA-1000 sold by Shibata Rikagaku Kikai Kabushiki Kaisha.

Munsell value: Measurement was made on sample pigments tapped on a glass cell using Minolta chroma meter Model CR-200.

MEASUREMENT OF LIGHT TRANSMISSION

The pigments of Example 1 calcined at varying temperatures were tested for light transmission properties.

1.57 g of sample pigment was intimately dispersed in a mixture of 21.8 g of nitrocellulose lacquer (note 1), 10.4 g of solvent mixture (note 2) and 2.1 g of dibutyl phathalate in a paint conditioner for 1 hour. This composition was applied on a polypropylene film using a 1.5 mil applicator and dried at room temperature overnight.

Note 1. Nitrocellulose lacquer

| Nitrocellulose | 10 parts by weight |
|---|---|
| Butyl acetate | 9 parts by weight |
| Ethyl acetate | 6 parts by weight |
| Ethylcellosolve | 3 parts by weight |
| Toluene | 8 parts by weight |

Note 2. Solvent Mixture

| Butyl acetate | 9 parts by weight |
|---|---|
| Ethyl acetate | 6 parts by weight |
| Ethylcellosolve | 3 parts by weight |
| Toluene | 9 parts by weight |

Figure 2:
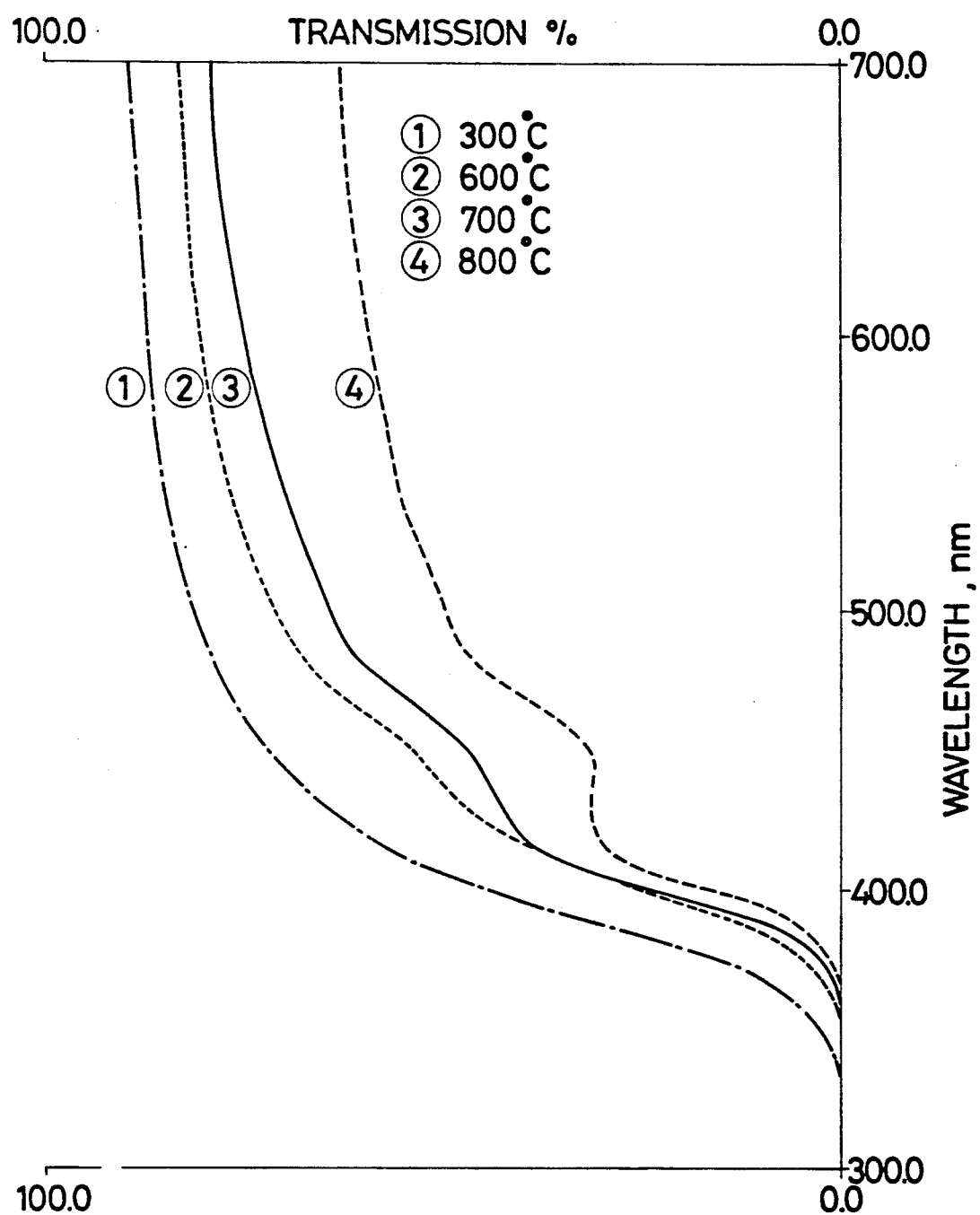
FIG. 2 shows light transmission curves of the pigment of Example 1 calcined at varying temperatures.

Percents transmission over a wavelength range between 300 nm and 700 nm were determined using specimen films thus prepared. The results are shown in FIG. 2.

Multilayer Metallic Coatings Incorporating the Pigment of this Invention a) The following ingredients were charged in a 400 ml plastic bottle and thoroughly dispersed using a paint shaker.

| $TiO_2$ microparticles produced in Example 11 or Comparative Example | 20.0 g |
|---|---|
| Acrylic varnish ACRYDIC 47-712 (note 3), 50% nonvolatile | 40.0 g |
| Solvent mixture (note 4) | 40.0 g |
| Zirconia beads of 0.8 mm diameter | 500.0 g | b) The resulting mill base obtained in step a) was mixed with the following ingredients.

| Acrylic varnish ACRYDIC 47-712 | 40.0 g |
|---|---|
| Melamin resin SUPER BEKKAMIN L-117 (note 5), 60% nonvolatile | 16.7 g |
| Solvent mixture (note 4) | 16.0 g | c) A metallic coating composition was prepared accordance to the following formulation.

| Aluminum flake paste ALUMIPASTE 7130 N (note 6), 64% nonvolatile | 40.0 g |
|---|---|
| Acrylic varnish ACRYDIC 47-712 | 160.0 g |
| Melamine resin SUPER BEKKAMIN L-117 | 33.3 g |
| Solvent mixture (note 4) | 135.0 g | d) 120 g of the composition in step b) and 35 g of the composition in step c) were intimately mixed in a paint mixer for 30 minutes to obtain a base coat composition.

e) A clear top coat composition was prepared according to the following formulation.

Figure 3B:
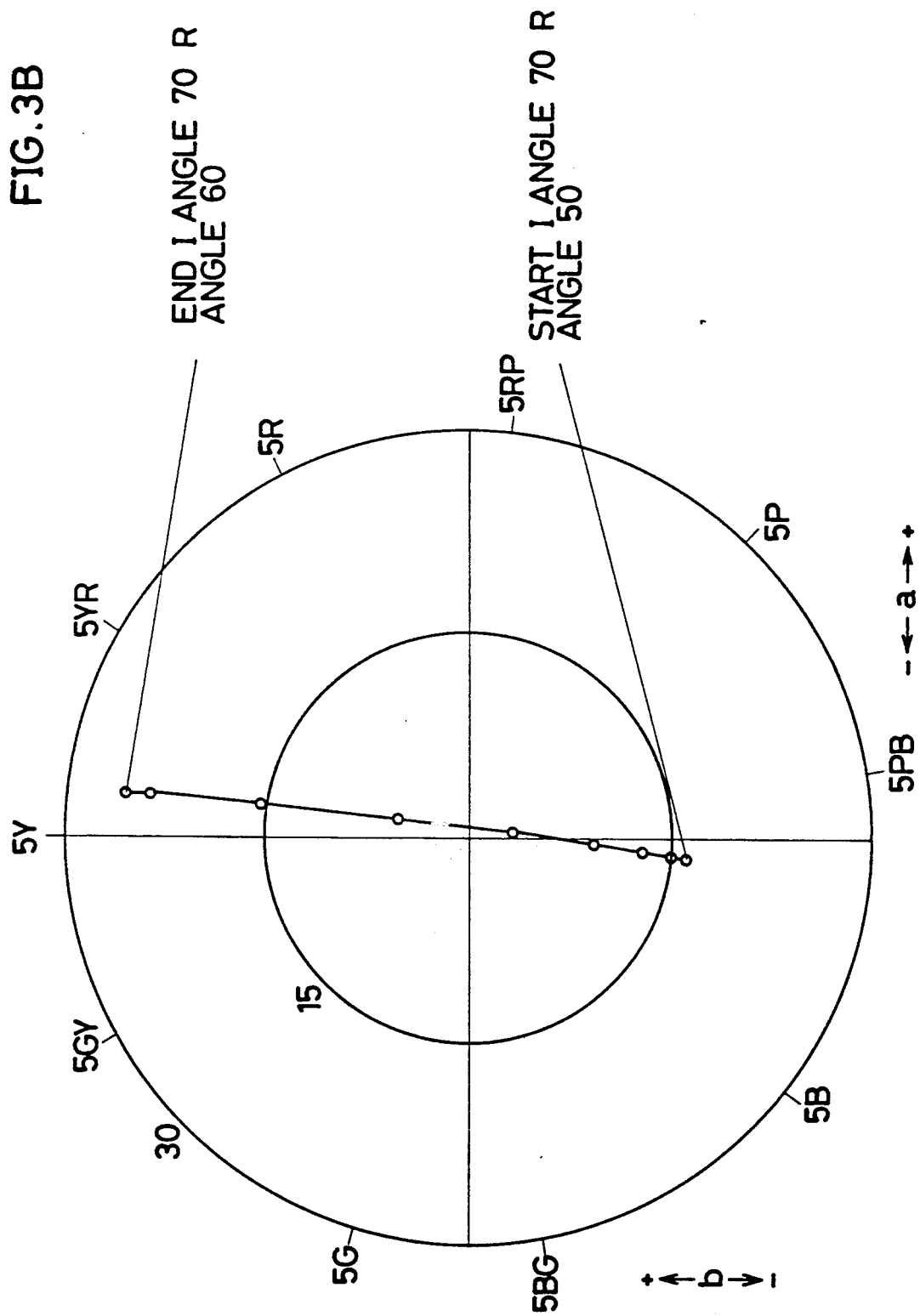

| Acrylic varnish ACRYDIC 44-179 (note 7) | 100.0 g |
|---|---|
| Melamin resin SUPER BEKKAMIN L-117 | 35.0 g | f) The base coat composition was sprayed on a steel plate to a dry film thickness of 25 microns and allowed to set at room temperature for 5 minutes. Then the clear top composition was sprayed thereon wet-on-wet, allowed to set for 8 minutes and baked both costs simultaneously at 140° C. for 30 minutes.

g) FIGS. 3A and 3B are chromaticity diagrams of the multilayer metallic coating films incorporating the colored $TiO_2$ microparticles produced in Example 11 and the colorless $TiO_2$ microiparticles produced in Comparative Example, respectively. The measurement was made using a gonio-photometric color measurement system GCMS-3 sold by Murakami Color Research Laboratories Co. Ltd., at an constant incident angle of 70° C. The color of reflected light was measured at varying angles. The results show that the coating film incorporating the pigment of Example 11 exhibit a variety of colors compared with the corresponding coating film incorporating the colorless $TiO_2$ microparticles of Comparative Example. This means that the coating film incorporating the pigment of the present invention will change its color delicately with the change in viewing angle. Furthermore, the results show that a bluish color has been diminished greatly on the ring side of the coating film incorporating the pigment of the present invention.

Note 3. Product of DAINIPPON INK AND CHEMICALS, INC.

Note 4. Toluene/xylene/ethyl acetate/butyl cellosolve = 5/2/2/1 by volume.

Note 5. Product of DAINIPPON INK AND CHEMICALS, INC.

Note 6. Product of TOYO ALUMINTUM K.K.

Note 7. Product of DAINIPPON INK AND CHEMICALS, INC.

What is claimed is:

1. A chromatic pigment comprising transparent core particles of titanium dioxide having a mean particle size from 0.01 to 0.1 μm coated thereon with a layer of an oxide of Ni, Co, Cu, Cr, Mn, V, W or a mixture of these oxides wherein the pigment substantially retains the transparency of the core particle.

2. The pigment of claim 1, wherein said coating layer amounts 1 to 30% as NiO, CoO or CuO $Cr_2O_3$, $MnO_2$, $V_2O_5$ or $WO_2$ by weight of the titanium dioxide particles.

3. The pigment of claim 2, wherein said oxide is nickel oxide.

4. The pigment of claim 2, wherein said oxide is cobalt oxide.

5. The pigment of claim 2, wherein said oxide is copper oxide.

6. The pigment of claim 2, wherein said oxide is chromium oxide.

7. The pigment of claim 2, wherein said oxide is manganese oxide.

8. The pigment of claim 2, wherein said oxide is vanadium oxide.

9. The pigment of claim 2, wherein said oxide is tungsten oxide.

10. The pigment of claim 1, wherein said titanium dioxide particles are of rutile type.

11. A method for producing a chromatic pigment comprising the steps of suspending transparent titanium dioxide microparticles having a mean particle size of 0.01 to 0.1 μm in an aqueous medium, adding a water-soluble metal compound of Ni, Co, Cu, Cr, Mn, V, W or a mixture of said compounds, hydrolyzing said metal compound and depositing the resulting metal hydroxide on said titanium dioxide particles, recovering and washing the particles, and calcining the resulting product at a temperature of 300° C. to 800° C.

12. The method of claim 11, wherein the amount of said water soluble metal compound range from 1 to 30% calculated as NiO, CoO, CuO, $Cr_2O_3$, $MnO_2$, $V_2O_5$, or $WO_2$ by weight of said titanium dioxide particles.

13. The method of claim 11 wherein said water-soluble metal compound is the chloride, sulfate or nitrate of Ni, Co, Cu, Cr, Mn or V, or ammonium tungstate.

14. The method of claim 11, wherein said hydrolyzing step includes adjusting the pH of said suspension at 8 to 9 with an alkali or acid.

15. A coating composition comprising:
   (a) 20 to 40% by weight of a film-forming synthetic resin;
   (b) 1 to 10% by weight of a metallic or metallic-like pigment;
   (c) 1 to 15% by weight of the colored $TiO_2$ microparticle pigment of claim 1; and
   (d) the balance being an organic volatile solvent for said film-forming synthetic resin, said composition being for use in finishing a substrate with a multilayer metallic coating comprising a base coat of said composition and a clear top coating applied thereon.

* * * * *